US011278586B2

(12) United States Patent
Tamura et al.

(10) Patent No.: US 11,278,586 B2
(45) Date of Patent: Mar. 22, 2022

(54) HIGHLY ABSORBABLE ORAL TYROSINE FORMULATION

(71) Applicant: Kao Corporation, Tokyo (JP)

(72) Inventors: Kotaro Tamura, Tochigi (JP); Masazumi Iwashita, Saitama (JP); Yoshihiko Minegishi, Utsunomiya (JP)

(73) Assignee: Kao Corporation, Tokyo (JP)

( * ) Notice: Subject to any disclaimer, the term of this patent is extended or adjusted under 35 U.S.C. 154(b) by 44 days.

(21) Appl. No.: 16/646,787

(22) PCT Filed: Sep. 21, 2018

(86) PCT No.: PCT/JP2018/035086
§ 371 (c)(1),
(2) Date: Mar. 12, 2020

(87) PCT Pub. No.: WO2019/059356
PCT Pub. Date: Jun. 28, 2019

(65) Prior Publication Data
US 2020/0261533 A1 Aug. 20, 2020

(30) Foreign Application Priority Data
Sep. 25, 2017 (JP) .............................. JP2017-183667

(51) Int. Cl.
| | |
|---|---|
| *A61K 38/05* | (2006.01) |
| *A61K 9/00* | (2006.01) |
| *A61P 25/00* | (2006.01) |
| *A61P 43/00* | (2006.01) |
| *C07K 5/06* | (2006.01) |
| *A23L 33/18* | (2016.01) |

(52) U.S. Cl.
CPC .............. *A61K 38/05* (2013.01); *A23L 33/18* (2016.08); *A61K 9/0056* (2013.01)

(58) Field of Classification Search
CPC ....... A23L 33/175; A23L 33/18; A61K 38/05; A61K 47/183; A61K 9/0053; A61K 9/0056; A61K 9/0095; A61K 9/00; A61P 25/00; A61P 43/00; C07K 5/06; C07K 5/06008; C07K 5/06121
See application file for complete search history.

(56) References Cited

U.S. PATENT DOCUMENTS

| | | |
|---|---|---|
| 5,036,052 A | 7/1991 | Ozeki et al. |
| 2011/0104334 A1 | 5/2011 | Nakahara et al. |
| 2012/0282243 A1 | 11/2012 | Endo et al. |

FOREIGN PATENT DOCUMENTS

| | | | |
|---|---|---|---|
| EP | 0646375 | A1 | 4/1995 |
| JP | 2-121928 | A | 5/1990 |
| JP | 7-149665 | A | 6/1995 |
| JP | 2003-063959 | A | 3/2003 |
| JP | 2010-029183 | A | 2/2010 |
| JP | 2016-014007 | A | 1/2016 |
| WO | WO 2009/03 8106 | A1 | 3/2009 |
| WO | WO 2011/078324 | A1 | 6/2011 |

OTHER PUBLICATIONS

Glycyl-L-Tyrosine from www.usp.org, pp. 1-4. 2014. (Year: 2014).*
Certificate for Glycyl-L-Tyrosine from www.usp.org, pp. 1-2. 2014. (Year: 2014).*
Stehle et al., "Parenteral Glycyl-L-Tyrosine Maintains Tyrosine Pools and Supports Growth and Nitrogen Balance in Phenylalanine-Deficient Rats," Nutrient Metabolism, 1996, 663-667. (Year: 1996).*
International Search Report (ISR) for PCT/JP2018/035086; I.A. fd Sep. 21, 2018, dated Dec. 18, 2018 from the Japan Patent Office, Tokyo, Japan.
International Preliminary Report on Patentability (IPRP), Chapter I of the Patent Cooperation Treaty, including the Written Opinion, for PCT/JP2018/035086; I.A. fd Sep. 21, 2018 dated Mar. 31, 2020, by the International Bureau of WIPO, Geneva, Switzerland.
Gelenberg, A., et al., "Tyrosine for depression" J Psychiatr Res. 1982;17(2):175-180. doi:10.1016/0022-3956(82)90019-x.
Banderet, L.E. et al., "Treatment with tyrosine, a neurotransmitter precursor, reduces environmental stress in humans." Brain Res Bull. 1989;22(4):759-762.doi: 10.1016/0361-9230(89)90096-8.
Esaki, K. et al., "Increased tyrosine in the brain and serum of mice by orally administering dipeptide SY." Biosci Biotechnol Biochem. 2013;77(4):847-849. doi:10.1271/bbb. 120747.
Maher, T.J. et al., "Use of parenteral dipeptides to increase serum tyrosine levels and to enhance catecholamine-mediated neurotransmission." J Pharm Sci. 1990;79(8):685-687. doi: 10.1002/jps. 2600790807.
U.S. Pharmacopeial Convention (USP) Safety Data Sheet, Material Name: Glycyl-L-Tyrosine, version: 02; anonymous, 5 pages, issued Jun. 27, 2013, revised Apr. 1, 2014.

* cited by examiner

*Primary Examiner* — Julie Ha
(74) *Attorney, Agent, or Firm* — Sterne, Kessler, Goldstern & Fox P.L.L.C.

(57) ABSTRACT

Provided is a tyrosine formulation excellent in bioabsorbability of tyrosine when ingested orally. An oral formulation with improved bioabsorbability of tyrosine, including glycyltyrosine or a salt thereof or a solvate thereof.

3 Claims, 1 Drawing Sheet

[FIG.1]
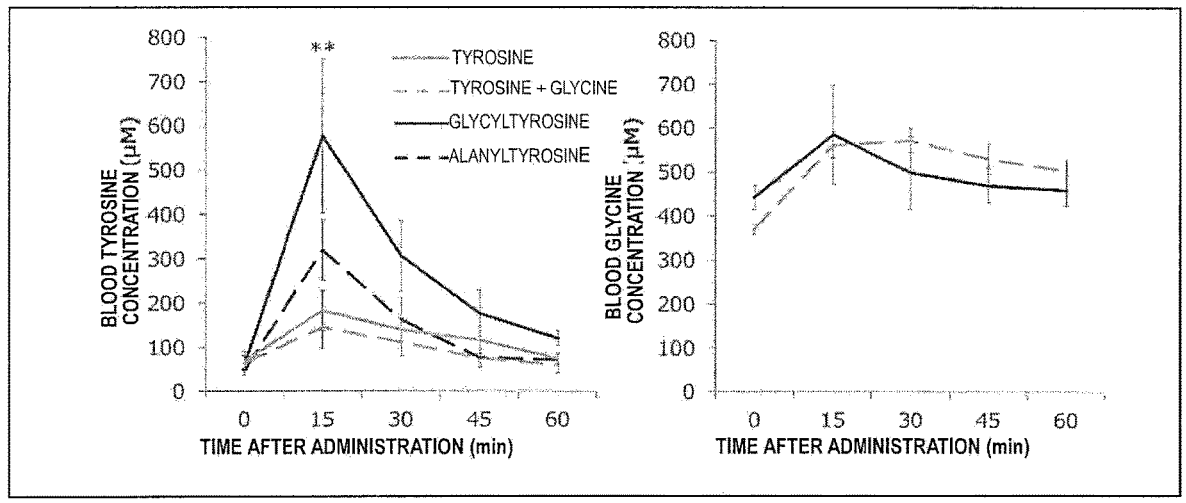
[FIG.2]
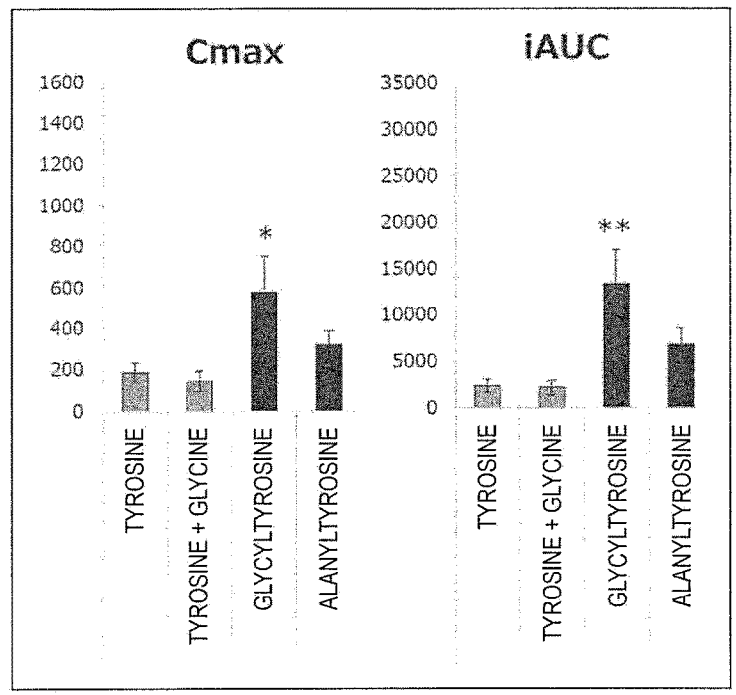

HIGHLY ABSORBABLE ORAL TYROSINE FORMULATION

FIELD OF THE INVENTION

The present invention relates to a highly absorbable oral tyrosine formulation with improved bioabsorbability of tyrosine.

BACKGROUND OF THE INVENTION

Tyrosine is a type of amino acid constituting protein, and is also used as a nutritional component such as amino acid infusion and oral nutrient. In addition, since tyrosine is a precursor of neurotransmitter dopamine in the brain, it is known to reduce stress and depressive symptoms (Non Patent Literatures 1 and 2) and is also used as a component of health foods such as supplements.

On the other hand, tyrosine is poorly water-soluble and is known to have low bioabsorbability. Against this, tyrosine solubility is improved by derivatizing tyrosine. For example, it has been reported that oral administration of alanyltyrosine rapidly increases the blood concentration of tyrosine (Patent Literature 1). However, it was not sufficient to increase bioavailability of tyrosine.

In addition, while tyrosine is difficult to be administered by drip infusion in the form of a free amino acid, a method of administering tyrosine by drip infusion as a dipeptide is also known (Patent Literature 2, etc.), but it is not a method that increases the blood concentration of tyrosine by oral ingestion.

Patent Literature 1: WO 2009/038106 A
Patent Literature 2: JP H2-121928 A
Non Patent Literature 1: Tyrosine for depression. J. Psychiat. Res. 1982-83 Vol. 17 No. 2 p 175-180
Non Patent Literature 2: Treatment with tyrosine, a neurotransmitter precursor, reduces environmental stress in human. Brain Res. Bull. 1989 Vol. 22 p 759-762

SUMMARY OF THE INVENTION

The present invention relates to the following 1) to 6).
1) An oral formulation with improved bioabsorbability of tyrosine, comprising glycyltyrosine or a salt thereof or a solvate thereof.
2) An agent for increasing a tyrosine concentration in the body comprising glycyltyrosine or a salt thereof or a solvate thereof as an active ingredient.
3) An agent for preventing or ameliorating a symptom resulting from depletion of a neurotransmitter in the brain, comprising glycyltyrosine or a salt thereof or a solvate thereof as an active ingredient.
4) A method for improving bioabsorbability of tyrosine, comprising orally ingesting or administering glycyltyrosine or a salt thereof or a solvate thereof.
5) A method for increasing a tyrosine concentration in the body, comprising orally ingesting or administering glycyltyrosine or a salt thereof or a solvate thereof.
6) A method for preventing or ameliorating a symptom resulting from depletion of a neurotransmitter in the brain, comprising orally ingesting or administering glycyltyrosine or a salt thereof or a solvate thereof.

BRIEF DESCRIPTION OF DRAWINGS

FIG. 1 is a graph showing the blood tyrosine concentration after administration of formulation.

FIG. 2 is a graph showing the maximum blood concentration (Cmax) and the area under the increased blood concentration-time curve (iAUC) after administration of the formulation.

DETAILED DESCRIPTION OF THE INVENTION

The present invention is to provide a tyrosine formulation that is excellent in bioabsorbability of tyrosine when ingested orally.

The present inventors have studied in view of the above problems, and found that when glycyltyrosine that is a dipeptide derivative of tyrosine is administered orally, bioabsorbability of tyrosine is improved markedly and the effect of glycyltyrosine is superior to that of alanyltyrosine.

According to the present invention, migration to blood of tyrosine that has been known to have low bioavailability by oral ingestion can be enhanced. Therefore, it is possible to efficiently exhibit physiological actions of tyrosine with a smaller intake.

In the oral formulation with improved bioabsorbability of tyrosine of the present invention ("highly absorbable oral tyrosine formulation"; hereinafter abbreviated as "tyrosine formulation"), "glycyltyrosine" is a dipeptide represented by the following formula (1), and the tyrosine that is a constituent amino acid thereof may be any of L-form, D-form, and DL-form, but L-form is preferred.

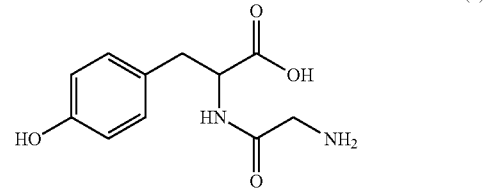

(1)

Examples of the salt of glycyltyrosine include an acid addition salt, a metal salt, an ammonium salt, and an organic amine addition salt.

Examples of the acid addition salt include an inorganic acid salt such as a hydrochloride, a sulfate, a nitrate and a phosphate, and an organic acid salt such as an acetate, a maleate, a fumarate, a citrate, a malate, a lactate, an α-ketoglutarate, a gluconate and a caprylate.

Examples of the metal salt include a salt of alkali metal (potassium, sodium, etc.), a salt of alkaline earth metal (calcium, magnesium, etc.), an aluminum salt, and a zinc salt.

Examples of the ammonium salt include a salt such as ammonium and tetramethylammonium.

Examples of the organic amine addition salt include a salt such as triethylamine, methylamine, dimethylamine, cyclopentylamine, benzylamine, phenethylamine, piperidine, monoethanolamine, diethanolamine, tris(hydroxymethyl) aminomethane, lysine, arginine, and N-methyl-D-glucamine.

Examples of the solvate include a solvate with water and an alcohol solvent (for example, ethanol), and preferred is a hydrate.

Glycyltyrosine in the present invention may be one produced by any production method such as a chemical synthesis method, a protein hydrolysis method, an enzyme method, or a fermentation method.

Examples thereof include a method of enzymatically hydrolyzing a natural protein having the amino acid sequence to obtain glycyltyrosine, and a chemical synthesis method described in Berichte der Deutschen Chemischen Gesellschaft, page 2486 (1904).

Moreover, a commercial product sold by, for example, Evonik Japan Co., Ltd., Tokyo Chemical Industry Co., Ltd., or Wako Pure Chemical Industries, Ltd. can also be used for glycyltyrosine or a salt thereof or a solvate thereof in the present invention.

As shown in the examples below, oral administration of glycyltyrosine improves bioabsorbability of tyrosine markedly as compared to oral administration of tyrosine, and the action of glycyltyrosine is superior to that of alanyltyrosine.

Therefore, a formulation containing glycyltyrosine or a salt thereof or a solvate thereof can be an oral formulation with improved bioabsorbability of tyrosine (highly absorbable oral tyrosine formulation).

The "oral formulation with improved bioabsorbability of tyrosine" means in detail, a formulation that is absorbed rapidly into a living body to increase the tyrosine concentration in the body, in the case where the formulation is administered orally to a human or non-human animal as compared to the case where tyrosine itself is administered.

The improvement of bioabsorbability or the increase in the tyrosine concentration in the body can be evaluated by measuring the maximum blood concentration (Cmax) after administration of the formulation and the area under the increased blood concentration-time curve (iAUC: increase area under the curve) after a certain period of administration.

The tyrosine formulation of the present invention is produced by mixing glycyltyrosine or a salt thereof or a solvate thereof with a pharmaceutically acceptable carrier as necessary, and using a method known in the art (for example, a granulation method such as fluidized bed granulation, agitation granulation, extrusion granulation, rolling granulation, airflow granulation, compression molding granulation, pulverization granulation, spray granulation and injection granulation, a coating method such as pan coating, fluidized bed coating and dry coating, a swelling method such as puff drying, an excess steam method, a foam mat method and a microwave heating method, and an extrusion method such as extrusion granulator and extruder), and provided as various formulations (for example, a pharmaceutical formulation, and a food formulation such as supplement).

Examples of the pharmaceutically acceptable carrier include a sugar such as lactose, sucrose, glucose, sucrose, mannitol and sorbitol, a starch of, for example, potato, wheat and corn, an inorganic substance such as calcium carbonate, calcium sulfate, sodium bicarbonate and sodium chloride, an excipient such as crystalline cellulose, powdered glycyrrhiza and powdered gentian, a disintegrant such as starch, agar, gelatin powder, crystalline cellulose, carmellose sodium, calcium carbonate, sodium bicarbonate and sodium alginate, a lubricant such as magnesium stearate, talc, hydrogenated vegetable oil, macrogol and silicone oil, a binder such as polyvinyl alcohol, hydroxypropyl cellulose, methyl cellulose, ethyl cellulose, carmellose, gelatin and starch paste, and a surfactant such as a fatty acid ester, and a plasticizer such as glycerin.

Moreover, in the formulation, for example, a coloring agent, a preservative, a flavor, a flavoring agent, a sweetening agent and another medicinal ingredient can be further contained as needed.

When formed as a food formulation, for example, a sweetener, a colorant, a preservative, a thickening stabilizer, an antioxidant, a color former, a bleaching agent, a fungicide, a gum base, a bittering agent, an enzyme, a gloss agent, an acidulant, a seasoning, an emulsifier, a reinforcing agent, a manufacturing agent, flavor, and a spice extract that are approved for use as a food additive can be appropriately blended.

Examples of the formulation form of the tyrosine formulation of the present invention include a solid formulation such as powders, tablets, granules, pills, pellets and capsules, and a liquid formulation such as suspension, emulsion, infusion/decoction, syrup, liquid, elixir, extract, tincture and fluid extract.

Moreover, in the case of the food formulation, for example, it can be in the form of powdered food, sheet-like food, capsule food, tablet-like food, liquid food, or drink.

The content of glycyltyrosine or a salt thereof or a solvate thereof in the tyrosine formulation of the present invention is appropriately selected, for example, according to the formulation form, administration or ingestion method, and effects expected by administration or ingestion, and it is usually 0.01% by mass or more, preferably 0.5% by mass or more, more preferably 1% by mass or more, and further preferably 5% by mass or more, and 90% by mass or less, preferably 80% by mass or less, more preferably 70% by mass or less, and further preferably 60% by mass or less, in terms of glycyltyrosine. Further, the content is from 0.01 to 90% by mass, preferably from 0.5 to 80% by mass, more preferably from 1 to 70% by mass, and further preferably from 5 to 60% by mass.

When the tyrosine formulation of the present invention is administered or ingested into a living body, the active ingredient glycyltyrosine is rapidly degraded into tyrosine in the body, and the tyrosine concentration in the body is increased, to thereby exhibit the physiological activity of tyrosine rapidly.

Examples of the physiological actions of tyrosine include supplementation of a neurotransmitter in the brain (a catecholamine such as dopamine, noradrenaline, and adrenaline), by converting it into the neurotransmitter in the brain.

Therefore, the tyrosine formulation of the present invention can be used for preventing or ameliorating a symptom resulting from lowering of the tyrosine concentration in the body or depletion of a neurotransmitter in the brain, for example, a symptom such as fatigue, depression, drowsiness, poor concentration, reduced attention, and reduced motivation, as an agent for increasing the tyrosine concentration in the body, further as an agent for preventing or ameliorating a symptom resulting from depletion of a neurotransmitter in the brain.

The dose or intake of the tyrosine formulation of the present invention varies depending on, for example, the administration or ingestion form, and the age and the body weight of a person to be administered or person who ingests the tyrosine formulation, but is usually 1 mg or more, preferably 10 mg or more, and more preferably 100 mg or more, and 4000 mg or less, preferably 2000 mg or less, and more preferably 1000 mg or less, in terms of glycyltyrosine, per day for an adult. Further, it is from 1 to 4000 mg, preferably from 10 to 2000 mg, and more preferably from 100 to 1000 mg.

Such administration or ingestion can be performed once a day or divided into several times.

The subject of administration or ingestion of the tyrosine formulation of the present invention is preferably a human, but it may be a non-human animal (mammals, birds, reptiles, amphibians, fish, etc.). Preferable examples of the subject include humans who are deficient in the tyrosine concentration in the body or lack a neurotransmitter in the brain, and humans who expect prevention or amelioration of a symptom resulting from lowering of the tyrosine concentration in the body or depletion of a neurotransmitter in the brain, for example, a symptom such as fatigue, depression, drowsiness, poor concentration, reduced attention, and reduced motivation.

Regarding the above-described embodiment, the following aspects are further disclosed in the present invention.

<1> An oral formulation with improved bioabsorbability of tyrosine, comprising glycyltyrosine or a salt thereof or a solvate thereof.

<2> The formulation of <1>, wherein the formulation is a liquid or solid formulation.

<3> The formulation of <2>, wherein the formulation is a food formulation.

<4> An agent for increasing a tyrosine concentration in the body comprising glycyltyrosine or a salt thereof or a solvate thereof as an active ingredient.

<5> An agent for preventing or ameliorating a symptom resulting from depletion of a neurotransmitter in the brain, comprising glycyltyrosine or a salt thereof or a solvate thereof as an active ingredient.

<6> A method for improving bioabsorbability of tyrosine, comprising orally ingesting or administering glycyltyrosine or a salt thereof or a solvate thereof.

<7> The method of <6>, wherein the orally ingesting or administering is ingesting or administering a liquid or solid formulation.

<8> The method of <6>, wherein the orally ingesting or administering is ingesting a food formulation.

<9> A method for increasing a tyrosine concentration in the body, comprising orally ingesting or administering glycyltyrosine or a salt thereof or a solvate thereof.

<10> A method for preventing or ameliorating a symptom resulting from depletion of a neurotransmitter in the brain, comprising orally ingesting or administering glycyltyrosine or a salt thereof or a solvate thereof.

<11> In any one of the formulations of <1> to <3> and <7> to <8>, or the agent of <4> or <5>, a content of glycyltyrosine or a salt thereof or a solvate thereof in the tyrosine formulation is usually 0.01% by mass or more, preferably 0.5% by mass or more, more preferably 1% by mass or more, and further preferably 5% by mass or more, and 90% by mass or less, preferably 80% by mass or less, more preferably 70% by mass or less, and further preferably 60% by mass or less, in terms of glycyltyrosine; and further, the content is from 0.01 to 90% by mass, preferably from 0.5 to 80% by mass, more preferably from 1 to 70% by mass, and further preferably from 5 to 60% by mass.

<12> In <1> to <10>, the dose or intake of glycyltyrosine or a salt thereof or a solvate thereof or a formulation comprising the same is usually 1 mg or more, preferably 10 mg or more, and more preferably 100 mg or more, and 4000 mg or less, preferably 2000 mg or less, and more preferably 1000 mg or less, in terms of glycyltyrosine, per day for an adult; and further, is from 1 to 4000 mg, preferably from 10 to 2000 mg, and more preferably from 100 to 1000 mg.

<13> Use of glycyltyrosine or a salt thereof or a solvate thereof for producing an oral formulation with improved bioabsorbability of tyrosine.

<14> Glycyltyrosine or a salt thereof or a solvate thereof, wherein the glycyltyrosine or the salt thereof or the solvate thereof is used orally for improving bioabsorbability of tyrosine.

<15> A method for non-therapeutically orally using glycyltyrosine or a salt thereof or a solvate thereof, for improving bioabsorbability of tyrosine.

<16> Use of glycyltyrosine or a salt thereof or a solvate thereof, for producing an agent for increasing a tyrosine concentration in the body.

<17> Glycyltyrosine or a salt thereof, or a solvate thereof, for increasing a tyrosine concentration in the body.

<18> A method for non-therapeutic use of glycyltyrosine or a salt thereof or a solvate thereof, for increasing a tyrosine concentration in the body.

<19> Use of glycyltyrosine or a salt thereof or a solvate thereof, for producing an agent for preventing or ameliorating a symptom resulting from depletion of a neurotransmitter in the brain.

<20> Glycyltyrosine or a salt thereof or a solvate thereof, for preventing or ameliorating a symptom resulting from depletion of a neurotransmitter in the brain.

<21> A method for non-therapeutic use of glycyltyrosine or a salt thereof or a solvate thereof, for preventing or ameliorating a symptom resulting from depletion of a neurotransmitter in the brain.

EXAMPLES

Hereinafter, the present invention will be described in more detail with reference to Examples and Reference Examples, but the present invention is not limited thereto.

Example 1: Effect of Improving Bioabsorbability of Tyrosine by Oral Administration of Glycyltyrosine (1) Method C57B6J Mice (CLEA Japan, Inc., 8 weeks old, male) were acclimatized for 1 week, and then the mice were divided into 4 groups with similar body weights (N=4 for each group). Each of amino acids dissolved in water was orally administered to the mice by sonde at the following dose in Table 1. Venous blood was collected from the fundus using a heparin-treated micro hematocrit tube (VITREX) under isoflurane anesthesia before administration and 15, 30, 45, and 60 minutes after administration. These were centrifuged (8,000×g, 10 minutes, 4° C.) to obtain plasma. Thereafter, a 15% by mass of aqueous sulfosalicylic acid solution which was three times amount of the plasma was added thereto, mixed, and centrifuged (8,000×g, 10 minutes, 4° C.) to remove the protein, and the obtained plasma was used as a sample for analysis. Quantification of amino acids in the sample for analysis was performed using LC-MS/MS. Infinity 1290 (Agilent) was used for liquid chromatography, and 3200 QTRAP (AB Sciex) was used for mass spectrometry.

A tyrosine administration group and a tyrosine and glycine (each equimolar amount) mixed administration group were set as controls for the glycyltyrosine administration group. An alanyltyrosine administration group was also set for effect comparison. Each administered substance used in this experiment is listed in Table 2.

TABLE 1

| Administered substance | Dose |
| --- | --- |
| Tyrosine | 0.55 mmol/kg Body weight |
| Tyrosine + Glycine | 0.55 mmol/kg Body weight each |
| Glycyltyrosine | 0.55 mmol/kg Body weight |
| Alanyltyrosine | 0.55 mmol/kg Body weight |

TABLE 2

| Administered substance | Product name | Place of purchase |
| --- | --- | --- |
| Tyrosine | L-Tyrosine | AJINOMOTO CO., INC. |
| Tyrosine + Glycine | AHS Glycine | AJINOMOTO CO., INC. |
| Glycyltyrosine | Glycyl-L-tyrosine dihydrate | Evonik Japan Co., Ltd. |
| Alanyltyrosine | L-Alanyl-L-tyrosine | Tokyo Chemical Industry Co., Ltd. |

(2) Results

1. Blood Tyrosine Concentration

At any time after administration, glycyltyrosine and alanyltyrosine were not detected in the plasma (results not shown).

Changes with time of the blood tyrosine concentration in the tyrosine administration group, the tyrosine and glycine mixed administration group, the glycyltyrosine administration group and the alanyltyrosine administration group, and changes with time of the blood glycine concentration of the tyrosine and glycine mixed administration group and the glycyltyrosine administration group are shown in FIG. 1. All values are presented as mean±standard error. Statistical analysis was performed by two-way repeated analysis of variance followed by Dunnett's post hoc test (**; $p<0.01$, showing significance to the tyrosine 0.55 mmol/kg body weight administration group).

As compared with the tyrosine administration group, only the glycyltyrosine administration group showed a significantly higher blood tyrosine concentration at 15 minutes after sample administration (FIG. 1). On the other hand, no significant difference was observed in the blood glycine concentration between the tyrosine and glycine mixed administration group and the glycyltyrosine administration group at any time after administration (FIG. 1).

2. Maximum Blood Concentration (Cmax) and Area Under Increased Blood Concentration-Time Curve (iAUC)

The maximum blood concentration (Cmax) after sample administration and the area under the increased blood concentration-time curve (iAUC: increase area under the curve) until 60 minutes after administration that were calculated based on the blood tyrosine concentration of each administration group are shown in FIG. 2. All values are presented as mean±standard error. Statistical analysis was performed by one-way analysis of variance followed by Dunnett's post hoc test (*; $p<0.05$, **; $p<0.01$, showing significance to the tyrosine administration group).

The Cmax and iAUC showed significantly high values only in the glycyltyrosine administration group as compared to those in the tyrosine administration group (FIG. 2).

From the above results, it is considered that the extent of improving bioabsorbability of tyrosine by oral administration/ingestion of glycyltyrosine is superior to that of oral administration/ingestion of alanyltyrosine. Glycyltyrosine and alanyltyrosine are known to have high solubility as compared to tyrosine, and the solubility thereof in water at 20° C. is about 75 times and about 36 times that of tyrosine, respectively (Fust et al., (2001) J. Nutr.). However, the dose of 0.55 mmol/kg body weight was an amount equivalent to 10 times the solubility of tyrosine, resulting that both glycyltyrosine and alanyltyrosine in the administration sample were completely dissolved in water. In spite of this, an excellent action of improving bioabsorbability of tyrosine was confirmed only in the oral administration/ingestion of glycyltyrosine. Therefore, the action is considered not due to the improvement in solubility, but an effect unique to glycyltyrosine.

What is claimed is:

1. A method for improving bioabsorbability of orally-delivered tyrosine in a subject, comprising orally ingesting by the subject, or orally administering to the subject, glycyltyrosine or a salt thereof or a solvate thereof,
    wherein the subject is deficient in tyrosine,
    wherein the orally ingesting or orally administering increases the maximum blood tyrosine concentration ($C_{max}$) of the subject as compared with the subject's $C_{max}$ obtained by orally ingesting or orally administering, respectively, free tyrosine; and
    wherein the orally ingesting or orally administering increases the area under the increased blood concentration-time curve (iAUC) of the subject as compared with the subject's iAUC obtained by orally ingesting or orally administering, respectively, free tyrosine.

2. The method according to claim 1, wherein the orally ingesting or orally administering comprises orally ingesting or orally administering a liquid or solid formulation of the glycyltyrosine or a salt thereof or a solvate thereof.

3. The method according to claim 1, wherein the orally ingesting or orally administering comprises ingesting a food formulation of the glycyltyrosine or a salt thereof or a solvate thereof.

* * * * *